US007547700B2

(12) United States Patent
Vacher et al.

(10) Patent No.: US 7,547,700 B2

(45) Date of Patent: Jun. 16, 2009

(54) ARYL-[4-HALO-4(HETEROARYLMETHYL AMINO)-METHYL]-PIPERIDIN-1-1YL]-METHANONE DERIVATIVES, METHODS FOR PRODUCTION AND USE THEREOF AS MEDICAMENTS

(75) Inventors: Bernard Vacher, Castres (FR); Bernard Bonnaud, Lagarrigue (FR); Jean-Louis Maurel, Castres (FR); Francis Colpaert, Puylaurens (FR)

(73) Assignee: PIERRE Fabre Medicament, Boulogne Billancourt (FR)

( * ) Notice: Subject to any disclaimer, the term of this patent is extended or adjusted under 35 U.S.C. 154(b) by 430 days.

(21) Appl. No.: 10/518,394

(22) PCT Filed: Jun. 18, 2003

(86) PCT No.: PCT/FR03/01873

§ 371 (c)(1), (2), (4) Date: Dec. 17, 2004

(87) PCT Pub. No.: WO03/106449

PCT Pub. Date: Dec. 24, 2003

(65) Prior Publication Data

US 2006/0100244 A1 May 11, 2006

(30) Foreign Application Priority Data

Jun. 18, 2002 (FR) .................................. 02 07470

(51) Int. Cl.
*A61K 31/501* (2006.01)

(52) U.S. Cl. .................. 514/252.03; 514/256; 514/269; 544/238; 544/242; 544/298; 544/334

(58) Field of Classification Search ................. 546/194; 514/256, 269, 252.03; 544/238, 242, 298, 544/334

See application file for complete search history.

(56) References Cited

U.S. PATENT DOCUMENTS 6,020,345 A * 2/2000 Vacher et al. ............... 514/318

6,448,268 B1 * 9/2002 Vacher et al. ............... 514/318

FOREIGN PATENT DOCUMENTS

WO WO 98 22459 5/1998

OTHER PUBLICATIONS

Grant R. Zimmermann "Multi-target therapeutics: when the whole is greater than the sum of the parts." Drug Discovery Today 2007, 12, 34-42.*

Borisy et. al. "Systematic discovery of multicomponent therapeutics" PNAS 2003, 100, 7977-7982.*

West, Anthony R., Solid State Chemistry and its Applications, Wiley, New York, 1988, pp. 358 & 365.*

Terry Kenakin and Ongun Onaran "The ligand paradox between affinity and efficacy: can you be there and not make a difference?" Trends in Pharmacological Sciences 2002, 23, 275-280.*

Raymond, John R "The recombinant 5-HT1A receptor: G protein coupling and signalling pathways." British Journal of Pharmacology, 1999, 127(8), 1751-1764.*

Norman, Andrew B. et. al. "[3H]Lysergic acid diethylamide (LSD): differential agonist and antagonist binding properties at 5-HT receptor subtypes in rat brain." Neurochemistry International 1989, 14(4), 497-504.*

Cammack, Richard Oxford Dictionary of Biochemistry and Molecular Biology, Oxford University Press: 2006, p. 234.*

"certain" The American Heritage Dictionary of the English Language: Fourth Edition. 2000, online "http://www.bartleby.com/61/39/C0213900.html" accessed May 20, 2008.*

Petit-Demouliere et. al. "Forced swimming test in mice: a review of antidepressant activity." Psychopharmacology 2005, 177, 245-255.*

International Search Report in corresponding PCT application No. PCT/FR03/001873.

* cited by examiner

*Primary Examiner*—Rita J Desai
*Assistant Examiner*—David K O'Dell
(74) *Attorney, Agent, or Firm*—Finnegan, Henderson, Farabow, Garrett & Dunner, LLP

(57) ABSTRACT

The invention relates to compounds of general formula (1) in which X and Y=a carbon with a bonded hydrogen atom (CH) or a nitrogen atom, A=a methyl, fluoromethyl, cyano, hydroxyl, methoxy group, or a chlorine or fluorine atom on condition that when A=methyl (CH3) and X and Y both=a carbon bonded to a hydrogen atom, then B=a chlorine atom, B=a chlorine or a fluorine atom, D=a hydrogen, chlorine, fluorine atom, or a cyano or trifluoromethyl group and E=a hydrogen, fluorine or chlorine atom.

12 Claims, No Drawings

ARYL-[4-HALO-4(HETEROARYLMETHYL AMINO)-METHYL]-PIPERIDIN-1-1YL]-METHANONE DERIVATIVES, METHODS FOR PRODUCTION AND USE THEREOF AS MEDICAMENTS

5-HT1$_A$ agonists may be useful for treating certain central nervous system disorders (*CNS Drugs* 1998, 10(5), 343-353). Although a very large number of compounds have been claimed as having agonist properties on receptors of the 5-HT1$_A$ subtype, only two are clinically available (i.e. buspirone: Europe and United States, and tandospirone: Japan). However, these two compounds belong to the same chemical family (i.e. arylpiperazine) and have relatively similar pharmacological profiles.

The contrast between the number of candidates and the number of clinically available compounds illustrates, inter alia, the limits of the pharmacological characterization of 5-HT1$_A$ agonists using criteria such as affinity, selectivity and standard pharmacodynamic criteria. On the other hand, the efficacy of the ligands on the 5-HT1$_A$ receptors is rarely reported. Now, it is becoming increasingly clear that the intrinsic activity of a ligand, and thus its efficacy on the 5-HT1$_A$ receptors, determines not only its therapeutic area of activity in the field of potential 5-HT1$_A$ indications, but also its level of activity in a given therapeutic indication (*Eur. J. Pharmacol.* 2001, 420, 103-112). Although, in theory, the intrinsic activity (and thus the efficacy) of a 5-HT1$_A$ ligand is an essential parameter, in practice, its measurement remains dependent on the experimental conditions used.

However, this situation has been exploited and forms the basis of the development of systems in which the relative efficacy of the 5-HT1$_A$ ligands may be evaluated with increased resolving power in certain regions of the intrinsic activity spectrum (*J. Pharmacol. Exp. Ther.* 2000, 292(2), 684-91; *Naunyn-Schmiedeberg's Arch. Pharmacol.* 1997, 356, 551-61). The use of said systems demonstrates two important features: the scope of the unexplored field of efficacy between antagonist and full agonist is vast; very few ligands have an efficacy greater than that of 8-OH-DPAT (8-hydroxy-2-di-n-propylaminotetralin), despite the profusion of ligands claimed as 5-HT1$_A$ agonists. It is remarkable, for example, that 8-OH-DPAT, which is considered as the reference 5-HT1$_A$ agonist, has mediocre efficacy compared with that of serotonin.

Given the large therapeutic potential of compounds having agonist activity for the 5-HT1$_A$ receptors and the absence of ligands whose efficacy approaches that of serotonin, the discovery of novel structures having 5-HT1$_A$ agonist properties superior to that of the known ligands is highly desirable. The Applicant has discovered that several compounds derived from aryl-{4-halo-4-[(heteroarylmethylamino)methyl]piperidin-1-yl}-methanone interact selectively with the serotoninergic receptors of the 5-HT1A subtype, on which they behave like effective agonists. As such, the compounds of the invention are therefore potentially useful for treating disorders sensitive to a serotoninergic regulation controlled by the 5-HT1$_A$ receptors. The list of disturbances, disorders and pathologies considered as sensitive to such a regulation is long; however, we are limiting the field of application of the present invention to the treatment of depression, dependence on certain substances and pain.

The closest prior art is represented by compounds of the pyridin-2-ylmethylamine type (WO 98/22459) corresponding to the following formula:

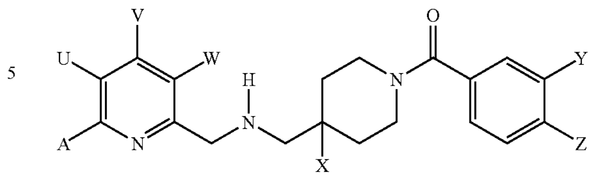

in which:

A represents, inter alia, a hydrogen atom;

U represents, inter alia, a methyl radical;

V represents, inter alia, a hydrogen atom;

W represents, inter alia, a hydrogen atom;

X represents, inter alia, a fluorine atom;

Y represents, inter alia, a chlorine atom;

Z represents, inter alia, a hydrogen, fluorine or chlorine atom.

The compounds under consideration are claimed as being selective 5-HT$_{1A}$ agonists, useful as antidepressants or analgesics.

The compounds claimed in patent WO 98/22459 and the compounds of the present invention thus differ in the nature of their nitrogenous heterocycle and/or the nature of the substituents borne by said heterocycle and/or by the nature of the halogen atom in position 4 of the piperidine ring and/or the nature of the substituents borne by the aryl group. The compounds of the invention, like those claimed in patent WO 98/22459, have strong affinity and are selective for the 5-HT1$_A$ receptors (with respect, in particular, to the dopaminergic receptors of the $D_2$ subtype). However, entirely surprisingly, the structural modifications introduced into the compounds of the invention give them an efficacy that is generally higher than that of the compounds described in WO 98/22459. Thus, for virtually equivalent affinity and selectivity, it is shown, in vitro, that the capacity of several compounds of the invention to activate an effector protein complex is higher than that of (3-chloro-4-fluorophenyl)(4-fluoro-4-{[(5-methylpyridin-2-ylmethyl)-amino]methyl}piperidin-1-yl)methanone (compound I-66), which is the most efficient agonist described in patent WO 98/22459. The major interest of the compounds of the invention thus lies in their particular and, to date unequalled, capacity to activate the receptors of the 5-HT1$_A$ subtype; this property is advantageous since it opens up new therapeutic perspectives in human clinical medicine in fields for which there is a great therapeutic need and for which the clinically available 5-HT1$_A$ agonists are not effective, for instance the treatment of depression, dependence on certain substances or pain.

More specifically, one subject of the present invention is the novel aryl-{4-halo-4-[(heteroarylmethylamino)-methyl]piperidin-1-yl}methanone derivatives which, in base form, correspond to the general formula (1):

(1)

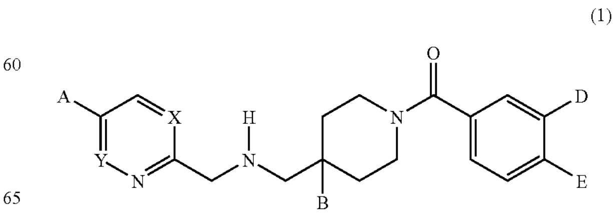

in which:

X represents a carbon atom linked to a hydrogen atom (CH) or a nitrogen atom;

Y represents a carbon atom linked to a hydrogen atom (CH) or a nitrogen atom;

A represents a methyl ($CH_3$), fluoromethyl ($CH_2F$), cyano (CN), hydroxyl (OH) or methoxy ($OCH_3$) radical or a chlorine or fluorine atom, with the proviso, however, that when A is a methyl radical ($CH_3$), and X and Y simultaneously represent a carbon atom linked to a hydrogen atom, then B necessarily represents a chlorine atom;

B represents a chlorine atom or a fluorine atom;

D represents a hydrogen atom, a chlorine atom, a fluorine atom, a cyano group (C≡N) or a trifluoromethyl group ($CF_3$);

E represents a hydrogen, fluorine or chlorine atom; the addition salts thereof and optionally the hydrates of the addition salts with pharmaceutically acceptable mineral acids or organic acids, and also the tautomeric forms thereof.

The invention is directed in particular toward the compounds of general formula (1) in which:

B and E each represent a fluorine atom;

D represents a chlorine atom.

The derivatives of general formula (1) may be obtained via the process described in scheme A.

Scheme A

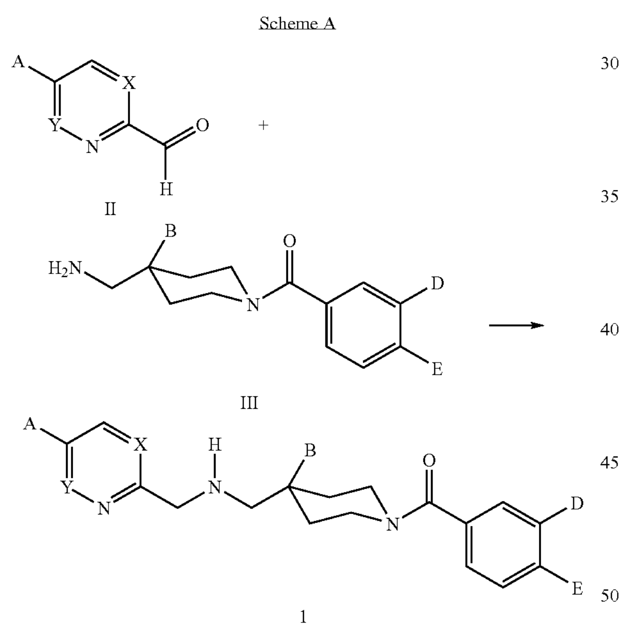

Scheme A

The compounds of formula (1) may be prepared via a reductive amination reaction between the aldehyde of formula (II) and the primary amine of formula (III) according to a method similar to the one described in patent WO 98/22459. The compounds of formula (I) are purified according to one or more methods chosen from crystallization and/or liquid-phase chromatographic techniques. They may then, if so desired, be salified using a pharmaceutically acceptable mineral or organic acid.

The preparation of the aldehydes of formula (II) depends on the nature of the groups X, Y and A. The preparation of the aldehydes (IIa1-6) in which X and Y are, together, a CH group and A represents a $CH_3$, CN, $OCH_3$ or OPMB group (the abbreviation "PMB" means p-methoxybenzyl), a chlorine atom or a fluorine atom, is described in the literature. Thus, the aldehyde (IIa-1) in which A is a $CH_3$ group may be prepared according to the method described in *Arch. Pharm. (Weinheim, Ger.)*, 1977, 310(2), 128-36.

The aldehyde (IIa-2) in which A is a CN group may be prepared according to WO 98/16526.

The aldehydes (IIa-3) and (IIa-4) in which A is an $OCH_3$ or OPMB group, respectively, may be prepared according to *Tetrahedron: Asymmetry* 2001, 12, 1047-51.

The aldehydes (IIa-5) and (IIa-6) in which A is a chlorine atom or a fluorine atom, respectively, may be prepared according to *J. Med. Chem.* 1970, 13(6), 1124-30.

The aldehyde (IIa-7) in which A is a $CH_2F$ group is, itself, prepared according to the process described in scheme B.

Scheme B

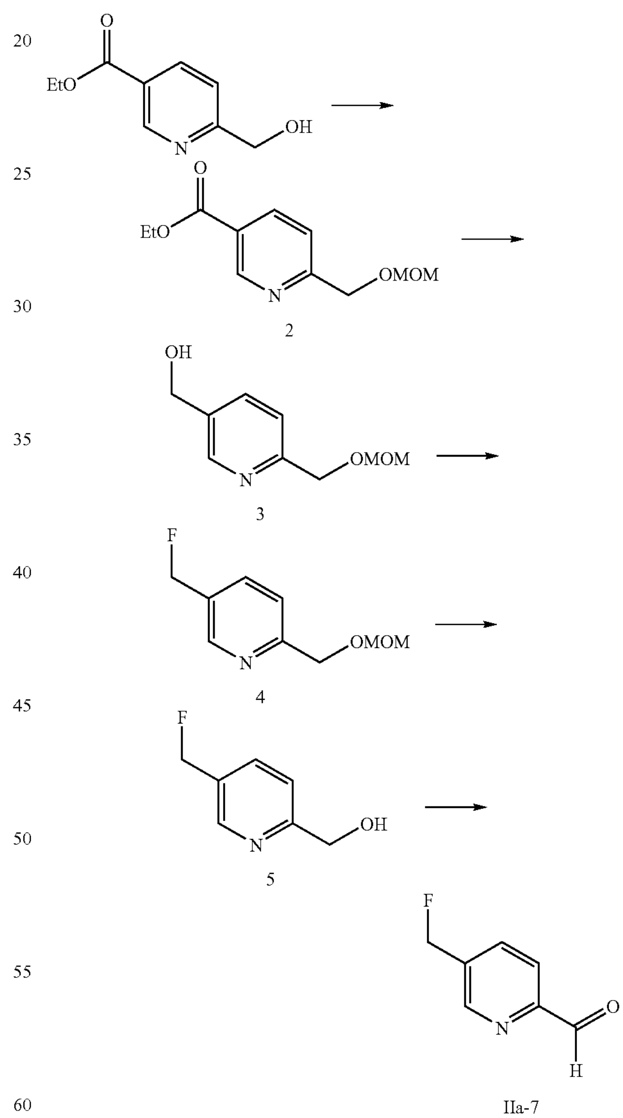

Scheme B

The preparation of the aldehyde (IIa-7) uses as starting material ethyl 6-hydroxymethylnicotinate (*Bio-org. Med. Chem. Lett.* 1996, 6(24), 3025-28). The primary alcohol function is protected in the form of the methoxymethyl ether and the ester function of the compound of formula (2) is then reduced using lithium aluminum hydride to give the alcohol of formula (3). The fluorine atom is introduced from the hydroxyl function using morpholinosulfur trifluoride in the presence of HF-pyridine complex in dichloromethane at low temperature. The cleavage of the methoxymethyl ether function from the compound of formula (4), performed in acidic medium, leads to the alcohol of formula (5), which is then oxidized to the desired aldehyde (IIa-7) using manganese dioxide ($MnO_2$) according to a method similar to that described in WO 98/22459.

The preparation of the aldehyde (IIb) in which X is a nitrogen atom, Y is a CH group and A represents a $CH_3$ group is described in patent U.S. Pat. No. 4,923,989.

The aldehyde (IIc) in which X is a CH group, Y is a nitrogen atom and A represents a $CH_3$ group may be prepared from 6-methylpyridazine-3-carbonitrile (*Heterocycles* 1986, 24(3), 793-7) via reduction of the cyano function using diisobutylaluminum hydride in tetrahydrofuran at low temperature according to a standard method well known to organic chemists. The preparation of the primary amines of formula (IIIa) in which B is a fluorine atom, D and E having the same meaning as previously, is performed according to a method similar to that described in WO 98/22459 and *J. Med. Chem.* 1999, 42(9), 1648-60.

The primary amines of formula (IIIb) in which B is a chlorine atom, D and E having the same meaning as previously, are prepared according to a method similar to that for the primary amines of formula (IIIa) *J. Med. Chem.* 1999, 42(9), 1648-60 and WO 98/22459. However, the step of opening of the spiro-epoxide is performed using a hydrochloric acid solution (4M) in dioxane rather than the hydrofluoric acid-pyridine complex as in the synthesis of the amines of the type (IIIa). The benzoic acids used as starting materials in the preparation of said spiro-epoxides are commercially available, except for 3-cyano-4-fluorobenzoic acid, which may be prepared according to the method described in *Tetrahedron Lett.* 1997, 38(18), 3131-34.

A subject of the invention is also pharmaceutical compositions containing as active principle at least one of the derivatives of general formula (1) or a salt thereof or hydrates of these salts in combination with one or more inert supports or other pharmaceutically acceptable vehicles.

The pharmaceutical compositions according to the invention may be, for example, compositions for oral, nasal, sublingual, rectal or parenteral administration. By way of example of compositions for oral administration, mention may be made of tablets, gel capsules, granules, powders and oral solutions or suspensions.

The formulations that are suitable for the chosen administration form are known and described, for example, in: Remington, The Science and Practice of Pharmacy, 19th Edition, 1995, Mack Publishing Company.

The effective dose of a compound of the invention varies as a function of numerous parameters, for instance the chosen route of administration, the weight, age, sex, degree of advancement of the pathology to be treated and the sensitivity of the individual to be treated. Consequently, the optimum dosage will be determined by the specialist in the field as a function of the parameters he deems pertinent. Although the effective doses of a compound of the invention may vary within large proportions, the daily doses may range between 0.01 mg and 100 mg per kg of body weight of the individual to be treated. A daily dose of a compound of the invention of between 0.05 mg and 50 mg per kg of body weight of the individual to be treated being, however, preferred.

The pharmaceutical compositions according to the invention are useful in the treatment of depression, dependence on certain substances and pain.

EXAMPLES

The following examples illustrate the invention, but do not limit it in any way.

In the examples below:

(i) the reaction progress is monitored by thin layer chromatography (TLC) and consequently the reaction times are given merely as a guide;

(ii) different crystalline forms may give different melting points, the melting points reported in the present patent application are those of the products prepared according to the described method and are uncorrected;

(iii) the structure of the products obtained according to the invention is confirmed by the nuclear magnetic resonance (NMR) spectra and elemental analysis, and the purity of the final products is checked by TLC;

(iv) the NMR spectra are recorded in the solvent indicated. The chemical shifts (δ) are given in parts per million (ppm) relative to tetramethylsilane. The multiplicity of the signals is indicated by: s, singlet; d, doublet; t, triplet; q, quartet; m, multiplet; b, broad;

(v) the various symbols for the units have their usual meaning: μg (microgram); mg (milligram); g (gram); ml (milliliter); ° C. (degrees Celsius); mmol (millimole); nmol (nanomole); cm (centimeter); nm (nanometer); min (minute); the pressures are given in millibar (mb);

(vi) the abbreviations have the following meaning:

m.p. (melting point); b.p. (boiling point); "room temperature" means a temperature of between 20° C. and 25° C.

Preparation of the intermediate (IIa-7)

Step 1: Ethyl 6-methoxymethoxymethylnicotinate (2)

Ethyl 6-hydroxymethylnicotinate (30 g, $1.65\times10^{-1}$ mol) is added dropwise to a suspension of sodium hydride (8 g, $1.98\times10^{-1}$ mol) in DMF (250 ml) cooled to −15° C. and maintained under a nitrogen atmosphere, and the mixture is stirred for 10 minutes and then cooled to −23° C. Chloromethyl methyl ether is then added dropwise, the mixture is stirred for 5 minutes after the end of the addition and then poured into 600 ml of ice-cold saturated $NaHCO_3$ solution. The mixture is extracted with petroleum ether and the combined organic phases are washed with water until neutral, and then with brine and dried over $Na_2SO_4$. After filtration, the solvent is evaporated off under vacuum and the residue is distilled (P: $4.2\times10^{-2}$ mb; b.p.: 120-130° C.). The title product is obtained in the form of a yellow oil (21 g), which is used in the following step without further purification.

Step 2: (6-methoxymethoxymethylpyridin-3-yl)methanol (3)

Compound (2) dissolved in tetrahydrofuran (100 ml) is added dropwise to a suspension of lithium aluminum hydride (9 g, $2.18\times10^{-1}$ mol) in tetrahydrofuran (200 ml) cooled to −80° C. and maintained under an inert atmosphere. The reaction mixture is stirred at −80° C. for 30 minutes after the end of the addition. $H_2O$ (18 ml), 10% NaOH in water (23 ml), THF (200 ml) and then $H_2O$ (53 ml) are added. The temperature is then returned to room temperature, followed by addition of ammonium acetate (20 g, $2.6\times10^{-1}$ mol) to the suspension. After 15 minutes, the reaction mixture is filtered through Celite and the filtrate is concentrated under vacuum. The residue is taken up in dichloromethane, the phases are separated by settling and the organic phase is dried over $Na_2SO_4$. After concentration under reduced pressure, the residue is purified by filtration through silica (eluent: 96/4 $CH_2Cl_2$/methanol). The product obtained (14.2 g) is used in the following step without further purification.

Step 3: 5-Fluoromethyl-2-methoxymethoxymethylpyridine (4)

A solution of 70% HF-pyridine complex (0.3 ml) is added to a solution of morpholinosulfur trifluoride (2 ml, $1.63\times10^{-2}$ mol) in dichloromethane (32 ml) cooled to −78° C. and maintained under an inert atmosphere, followed by dropwise addition of 1 g (5.4 mmol) of compound (3) as a solution in $CH_2Cl_2$ (10 ml). The mixture is stirred for 2 hours at −78° C. and then poured into saturated $NaHCO_3$ solution (75 ml). The aqueous phase is extracted with dichloromethane and the combined organic phases are washed with brine, dried over $Na_2SO_4$, filtered and concentrated under vacuum. The residue is bulb-to-bulb distilled (P: $4.7\times10^{-2}$ mb, b.p.: 110-130° C.). The title compound is isolated in the form of a colorless oil (0.3 g), which is used directly in the following step.

Step 4: (5-Fluoromethylpyridin-2-yl)methanol (5)

0.45 g of compound (4) dissolved in ethanol is added dropwise to a solution of hydrochloric acid (4.2N) in ethanol (5.5 ml) cooled to 0° C. at the end of the addition, the temperature of the mixture is returned to room temperature and stirring is continued for 12 hours. The reaction mixture is concentrated under vacuum and the residue obtained is washed with isopropyl ether. The ether phase is removed and the residue is taken up in a $CH_2Cl_2$/methanol solution (75/25) and then stirred over $Na_2CO_3$ (1.2 g). The mixture is filtered and the filtrate evaporated to give a colorless oil (0.3 g), which is used without further purification in the following step.

Step 5: 5-Fluoromethylpyridine-2-carbaldehyde (IIa-7)

Manganese dioxide (1.4 g) is added in a single portion to a solution of compound (5) (0.3 g) in chloroform (5 ml) at room temperature. The suspension is stirred vigorously for 7 hours and then diluted with chloroform and filtered through Celite. The filtrate is concentrated under vacuum and the yellow oil obtained (0.25 g) is used in its present form in the following reductive amination step.

$^1$H NMR ($CDCl_3$) δ: 5.53 (d, 2H); 7.90 (d, 1H); 8.01 (d, 1H); 8.79 (s, 1H); 10.09 (s, 1H).

Example 1

Preparation of (3-chloro-4-fluorophenyl)(4-fluoro-4-{[(5-hydroxypyridin-2-ylmethyl)amino]methyl}-piperidin-1-yl)methanone (1-1)

Step 1: Preparation of (4-{[(5-benzyloxypyridin-2-yl-methyl)amino]methyl}-4-fluoropiperidin-1-yl)(3-chloro-4-fluorophenyl)methanone (1-1a)

2.42 g (8.38 mmol) of (4-aminomethyl)-4-fluoropiperidin-1-yl)(3-chloro-4-fluorophenyl)methanone (IIIa-1) are added to a solution of 2 g (8.22 mmol) of the aldehyde (IIa-4) in 60 ml of 1,2-dichloroethane. Once the mixture is homogeneous, 5 g of 4 Å molecular sieves are added and the mixture is stirred for 30 minutes. 2.1 g of sodium triacetoxyborohydride (9.86 mmol) are then added portionwise and stirring is continued for 2 hours at room temperature. 10 ml of methanol are added and the reaction mixture is then filtered. The filtrate is concentrated under vacuum and the oil obtained is taken up in dichloromethane, washed with water then with brine, dried over $Na_2SO_4$, filtered and concentrated under reduced pressure. The residue is purified by chromatography on silica gel (eluent: 98/2 $CH_2Cl_2/CH_3OH$. The title product is obtained in the form of a colorless oil (3 g).

$^1$H NMR (DMSOd$_6$) δ: 1.62-191 (m, 4H); 2.33 (s, 1H); 2.67 (d, 2H); 3.05-3.39 (m, 3H); 3.75 (s, 5H); 4.25 (s, 1H); 5.07 (s, 2H); 6.94 (d, 2H); 7.32-7.51 (m, 6H); 7.66 (d, 1H); 8.24 (s, 1H)

Step 2: Preparation of (3-chloro-4-fluorophenyl)(4-fluoro-4-{[(5-hydroxypyridin-2-ylmethyl)amino]methyl}-piperidin-1-yl)methanone (1-1)

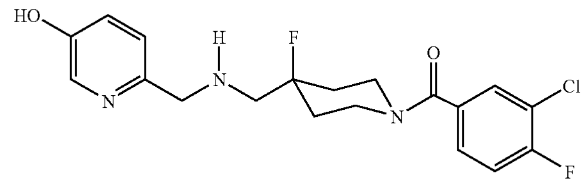

4.5 ml of trifluoroacetic acid (58 mmol) are added to a solution of 3 g (5.8 mmol) of compound (1-1a) in dichloromethane (50 ml) cooled to 0° C. and maintained under an inert atmosphere. After returning to room temperature, the mixture is stirred for 2 hours and then concentrated under vacuum. The residue is taken up in ethyl ether and the precipitate formed is filtered off and washed with ethyl ether. The precipitate is then dissolved in ethyl acetate and the solution is extracted with saturated $NaHCO_3$ solution. The organic phase is washed with brine, dried over $Na_2SO_4$, filtered and concentrated under vacuum to give 2.2 g of a pale yellow oil.

$^1$H NMR (DMSOd$_6$) δ: 1.66-1.98 (m, 4H); 2.22 (s, 1H); 2.67 (d, 2H); 3.15-3.50 (m, 3H); 3.71 (s, 2H); 4.20 (s, 1H); 7.12 (dd, 1H); 7.20 (d, 1H); 7.42-7.51 (m, 2H); 7.66 (dd, 1H); 8.03 (d, 1H); 9.69 (s, 1H).

Fumarate of the title compound:

m.p.: 225-227° C.

$C_{23}H_{24}ClF_2N_3O_6$: 511.91

Calculated %: C 53.97; H 4.73; N 8.21

Found %: C 53.73; H 4.97; N 8.01

$^1$H NMR (DMSOd$_6$) δ: 1.66 (m, 1H); 1.77 (m, 2H); 1.91 (m, 1H); 2.74 (d, 2H); 3.05 (m, 1H); 3.25 (m, 1H); 3.41 (m, 1H); 3.76 (s, 2H); 4.25 (m, 1H); 6.60 (s, 2H); 7.13 (dd, 1H); 7.23 (d, 1H); 7.45 (m, 2H); 7.66 (dd, 1H); 8.05 (d, 1H).

Example 2

Preparation of (3-chloro-4-fluorophenyl)-(4-fluoro-4-{[(5-cyanopyridin-2-ylmethyl)amino]methyl}-piperidin-1-yl)methanone (1-2)

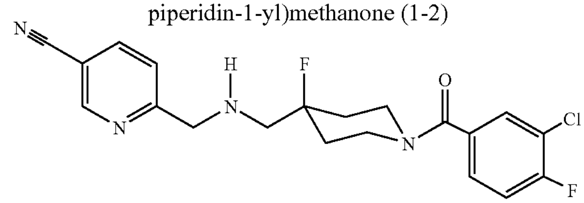

Working as in example 1, but replacing in step 1 the aldehyde (IIa-4) with 6-formylnicotinonitrile (IIa-2), the title compound is obtained.

Fumarate of the title compound:

m.p.: 170-172° C.

$C_{24}H_{23}ClF_2N_4O_5$: 520.93

Calculated %: C 55.34; H 4.45; N 10.76

Found %: C 55.32; H 4.50; N 10.73

$^1$H NMR (DMSOd$_6$) δ: 1.68 (m, 1H); 1.78 (m, 2H); 1.91 (m, 1H); 2.73 (d, 2H); 3.06 (m, 1H); 3.26 (m, 1H); 3.40 (m, 1H); 3.94 (s, 2H); 4.26 (m, 1H); 6.62 (s, 2H); 7.47 (m, 2H); 7.67 (m, 2H); 8.27 (dd, 1H); 8.94 (s, 1H).

Example 3

Preparation of (3-chloro-4-fluorophenyl)-(4-fluoro-4-{[(5-chloropyridin-2-ylmethyl)amino] methyl}piperidin-1-yl)methanone (1-3)

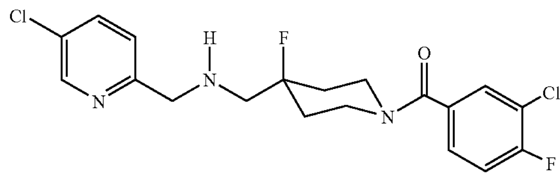

Working as in example 1, but replacing in step 1 the aldehyde (IIa-4) with 5-chloropyridine-2-carbaldehyde (IIa-5), the title compound is obtained.

Fumarate of the title compound:

m.p.: 160-162° C.

$C_{23}H_{23}Cl_2F_2N_3O_4$: 530.35

Calculated %: C 52.09; H 4.37; N 7.92

Found %: C 51.89; H 4.41; N 7.84

$^1$H NMR (DMSOd$_6$) δ: 1.65 (m, 1H); 1.78 (m, 2H); 1.78 (m, 1H); 2.72 (d, 2H); 3.06 (m, 1H); 3.25 (m, 1H); 3.39 (m, 1H); 3.85 (s, 2H); 4.25 (m, 1H); 6.62 (s, 2H); 7.44 (m, 1H); 7.49 (t, 2H); 7.66 (dd, 1H); 7.89 (dd, 1H); 8.54 (d, 1H).

Example 4

Preparation of (3-chloro-4-fluorophenyl)-(4-fluoro-4-{[(5-fluoromethylpyridin-2-ylmethyl)amino]-methyl}piperidin-1-yl)methanone (1-4)

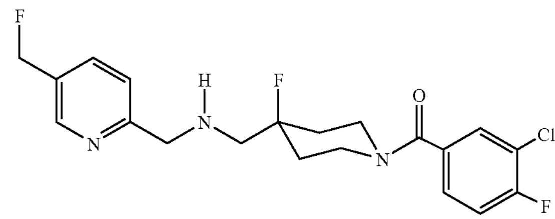

Working as in example 1, but replacing in step 1 the aldehyde (IIa-4) with 5-fluoromethylpyridine-2-carbaldehyde (IIa-7), the title compound is obtained.

Fumarate of the title compound:

m.p.: 157-159° C.

$C_{24}H_{25}ClF_3N_3O_5$: 527.92

Calculated %: C 54.60; H 4.77; N 7.96

Found %: C 54.42; H 4.65; N 7.75

$^1$H NMR (DMSOd$_6$) δ: 1.67 (m, 1H); 1.77 (m, 2H); 1.91 (m, 1H); 2.75 (d, 2H); 3.06 (m, 1H); 3.26 (m, 1H); 3.42 (m, 1H); 3.89 (s, 2H); 4.25 (m, 1H); 5.46 (d, 2H; J=48 Hz); 6.61 (s, 2H); 7.44 (m, 1H); 7.50 (d, 1H); 7.66 (dd, 1H); 7.85 (d, 1H); 8.57 (s, 1H).

Example 5

Preparation of (3-chloro-4-fluorophenyl)-(4-fluoro-4-{[(5-methylpyrimidin-2-ylmethyl)amino]-methyl}piperidin-1-yl)methanone (1-5)

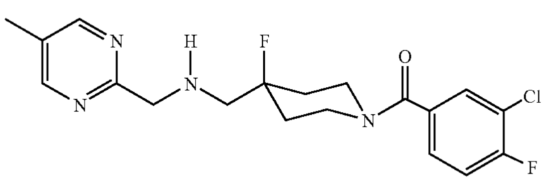

Working as in example 1, but replacing in step 1 the aldehyde (IIa-4) with 5-methylpyrimidine-2-carbaldehyde (IIb), the title compound is obtained.

Fumarate of the title compound:

m.p.: 105° C. (decomposition)

$C_{23}H_{25}ClF_2N_4O_5$: 510.93

Calculated %: C 53.39; H 4.85; N 10.38

Found %: C 53.20; H 5.11; N 10.52

$^1$H NMR (DMSOd$_6$) δ: 1.67-1.91 (m, 4H); 2.26 (s, 3H); 2.60 (d, 2H); 3.10-3.40 (m, 3H); 3.92 (s, 2H); 4.24 (s, 1H); 6.61 (s, 2H); 7.42-7.51 (m, 2H); 7.66 (d, 1H); 8.62 (s, 2H).

Example 6

Preparation of (3,4-dichlorophenyl)-(4-fluoro-4-{[(5-methylpyrimidin-2-ylmethyl)amino]-methyl}piperidin-1-yl)methanone (1-6)

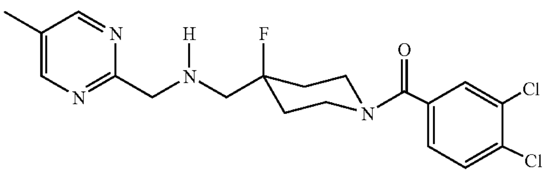

Working as in example 1, but replacing in step 1 the aldehyde (IIa-4) with 5-methylpyrimidine-2-carbaldehyde (IIb) and the primary amine (IIIa-1) with (4-aminomethyl-4-fluoropiperidin-1-yl)(3,4-dichlorophenyl)methanone (IIIa-2), the title compound is obtained.

Hemifumarate of the title compound:

m.p.: 161° C.

$C_{21}H_{23}Cl_2FN_4O_3$: 469.35

Calculated %: C 53.74; H 4.94; N 11.94

Found %: C 53.54; H 4.95 N 12.06

$^1$H NMR (DMSO$d_6$) δ: 1.65-1.98 (m, 4H); 2.25 (s, 3H); 2.80 (d, 2H); 3.07-3.51 (m, 3H); 3.89 (s, 2H); 4.24 (s, 1H); 6.61 (s, 1H); 7.40 (d, 1H); 7.70 (s, 1H); 7.71 (d, 1H); 8.62 (s, 2H).

Example 7

Preparation of (3-chloro-4-fluorophenyl)-(4-fluoro-4-{[(6-methylpyridazin-3-ylmethyl)amino]-methyl}piperidin-1-yl)methanone (1-7)

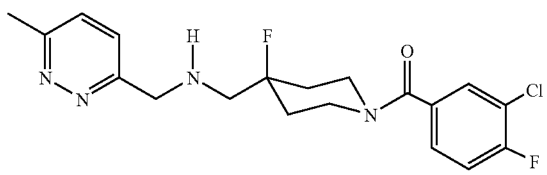

Working as in example 1, but replacing in step 1 the aldehyde (IIa-4) with 6-methylpyridazine-3-carbaldehyde (IIc), the title compound is obtained.

Dihydrochloride of the title compound:

m.p.: 205° C. (decomposition)

$C_{19}H_{23}Cl_3F_2N_4O$: 467.78

Calculated %: C 48.79; H 4.96; N 11.98

Found %: C 48.60; H 4.92; N 11.88

$^1$H NMR (DMSO$d_6$) δ: 1.79-2.04 (m, 4H); 2.68 (s, 3H); 3.07-3.51 (m, 3H); 3.35 (d, 2H); 4.26 (s, 1H); 4.53 (s, 2H); 7.43-7.46 (m, 1H); 7.52 (t, 1H); 7.67 (d, 1H); 7.76 (d, 1H); 7.92 (d, 1H).

Example 8

Preparation of (3,4-dichlorophenyl)-(4-fluoro-4-{[(6-methylpyridazin-3-ylmethyl)amino]-methyl}piperidin-1-yl)methanone (1-8)

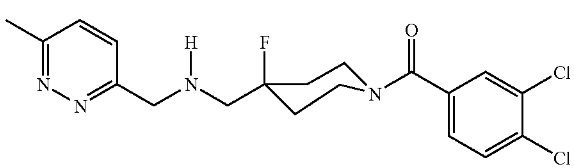

Working as in example 1, but replacing in step 1 the aldehyde (IIa-4) with 6-methylpyridazine-3-carbaldehyde (IIc) and the primary amine (IIIa-1) with (4-aminomethyl-4-fluoropiperidin-1-yl)(3,4-dichlorophenyl) methanone (IIIa-2), the title compound is obtained.

Oxalate of the title compound:

m.p.: 203° C. (decomposition)

$C_{21}H_{23}Cl_2FN_4O_5$: 501.35

Calculated %: C 50.31; H 4.62; N 11.18

Found %: C 50.34; H 4.69; N 11.14

$^1$H NMR (DMSO$d_6$) δ: 1.68-1.96 (m, 4H); 2.61 (s, 3H); 2.94 (d, 2H); 3.05-3.57 (m, 3H); 4.19 (s, 2H); 4.28 (s, 1H); 7.39 (d, 1H); 7.58 (d, 1H); 7.65. (d, 1H); 7.69-7.73 (m, 2H).

Example 9

Preparation of (3-chloro-4-fluorophenyl)-(4-chloro-4-{[(5-methylpyridin-2-ylmethyl)amino]-methyl}piperidin-1-yl)methanone (1-9)

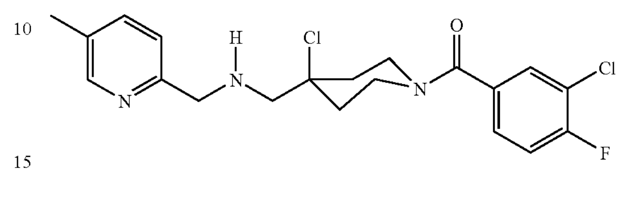

Working as in example 1, but replacing in step 1 the aldehyde (IIa-4) with 5-methylpyridine-2-carbaldehyde (IIa-1) and the primary amine (IIIa-1) with (4-aminomethyl-4-chloropiperidin-1-yl) (3-chloro-4-fluorophenyl)methanone (IIIb-1), the title compound is obtained.

Dihydrochloride of the title compound:

m.p.: 190° C. (decomposition)

$C_{20}H_{24}Cl_4FN_3O$: 483.35

Calculated %: C 49.71; H 5.01; N 8.70

Found %: C 49.62; H 4.99; N 8.72

$^1$H NMR (DMSO$d_6$) δ: 1.85-2.01 (m, 4H); 2.34 (s, 3H); 3.07-3.55 (m, 3H); 4.18 (s, 1H); 4.37 (s, 2H); 7.40-7.54 (m, 3H); 7.67 (d, 1H); 7.74 (d, 1H).

Example 10

Preparation of (4-fluorophenyl) (4-fluoro-4-{[(5-methylpyridin-2-ylmethyl)amino]methyl}piperidin-1-yl)methanone (1-10)

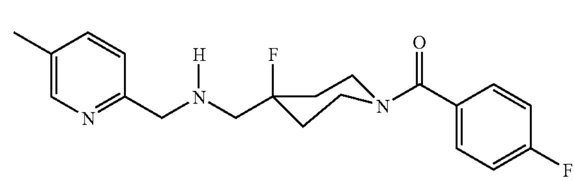

Working as in example 1, but replacing in step 1 the aldehyde (IIa-4) with 5-methylpyridine-2-carbaldehyde (IIa-1) and the primary amine (IIIa-1) with (4-aminomethyl-4-fluoropiperidin-1-yl)(4-fluorophenyl)methanone (IIIa-3), the title compound is obtained.

Fumarate of the title compound:

m.p.: 154-156° C.

$C_{24}H_{27}F_2N_3O_5$: 475.49

$^1$H NMR (DMSO$d_6$) δ: 1.66 (m, 1H); 1.77 (m, 2H); 1.86 (m, 1H); 2.27 (s, 3H); 2.75 (d, 2H); 3.08 (m, 1H); 3.23 (m, 1H); 3.43 (m, 1H); 3.83 (s, 2H); 4.26 (m, 1H); 6.42 (s, 2H); 7.29 (m, 3H); 7.48 (dd, 2H); 7.57 (d, 1H); 8.34 (s, 1H).

Example 11

Preparation of (3,4-difluorophenyl)-(4-fluoro-4-{[(5-methylpyridin-2-ylmethyl)amino]methyl} piperidin-1-yl)methanone (1-11)

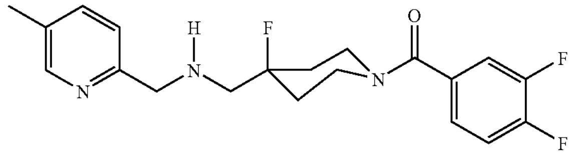

Working as in example 1, but replacing in step 1 the aldehyde (IIa-4) with 5-methylpyridine-2-carbaldehyde (IIa-1) and the primary amine (IIIa-1) with (4-aminomethyl-4-fluoropiperidin-1-yl)(3,4-difluorophenyl)methanone (IIIa-4), the title compound is obtained.

Fumarate of the title compound:

m.p.: 158° C.

$C_{24}H_{26}F_3N_3O_5$: 493.49

Calculated %: C 58.41; H 5.31; N 8.52

Found %: C 58.45; H 5.35; N 8.41

$^1$H NMR (DMSOd$_6$) δ: 1.64-1.91 (m, 4H); 2.27 (s, 3H); 2.73 (d, 2H); 3.06-3.41 (m, 3H); 3.82 (s, 2H); 6.61 (s, 2H); 7.26-7.31 (m, 1H); 7.31 (d, 1H); 7.48-7.58 (m, 3H); 8.33 (s, 1H).

Example 12

Preparation of (3-fluoro-4-chlorophenyl)-(4-fluoro-4-{[(5-methylpyridin-2-ylmethyl)amino]methyl}piperidin-1-yl)methanone (1-12)

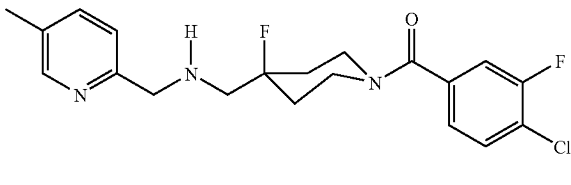

Working as in example 1, but replacing in step 1 the aldehyde (IIa-4) with 5-methylpyridine-2-carbaldehyde (IIa-1) and the primary amine (IIIa-1) with (4-aminomethyl-4-fluoropiperidin-1-yl)(3-fluoro-4-chlorophenyl)methanone (IIIa-5), the title compound is obtained.

Fumarate of the title compound:

m.p.: 150° C.

$C_{24}H_{26}ClF_2N_3O_5$: 509.94

Calculated %: C 56.53; H 5.14; N 8.24

Found %: C 56.58; H 5.24; N 8.19

$^1$H NMR (DMSOd$_6$) δ: 1.64-1.92 (m, 4H); 2.27 (s, 3H); 2.72 (d, 2H); 3.05-3.51 (m, 3H); 3.82 (s, 2H); 4.25 (s, 1H); 6.61 (s, 2H); 7.26-7.32 (m, 2H); 7.53 (d, 1H); 7.56 (d, 1H); 7.67 (m, 1H); 8.33 (s, 1H).

Example 13

Preparation of (3-cyano-4-fluorophenyl)-(4-fluoro-4-{[(5-methylpyridin-2-ylmethyl)amino]methyl}piperidin-1-yl)methanone (1-13)

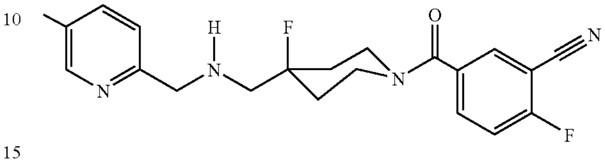

Working as in example 1, but replacing in step 1 the aldehyde (IIa-4) with 5-methylpyridine-2-carbaldehyde (IIa-1) and the primary amine (IIIa-1) with (4-aminomethyl-4-fluoropiperidin-1-yl)(3-cyano-4-fluorophenyl)-methanone (IIIa-6), the title compound is obtained.

Fumarate of the title compound:

m.p.: 175° C.

$C_{25}H_{26}F_2N_4O_5$: 500.51

Calculated %: C 59.99; H 5.24; N 11.19

Found %: C 59.99; H 5.32; N 10.85

$^1$H NMR (DMSOd$_6$) δ: 1.69-1.81 (m, 4H); 2.29 (s, 3H); 2.83 (d, 2H); 3.28-3.48 (m, 3H); 3.91 (s, 2H); 4.28 (s, 1H); 6.61 (s, 2H); 7.34 (d, 1H); 7.58-7.63 (m, 2H); 7.82-7.87 (m, 1H); 8.04 (m, 1H); 8.36 (s, 1H).

Example 14

Preparation of (3-trifluoromethylphenyl)-(4-fluoro-4-{[(5-methylpyridin-2-ylmethyl)amino]methyl}piperidin-1-yl)methanone (1-14)

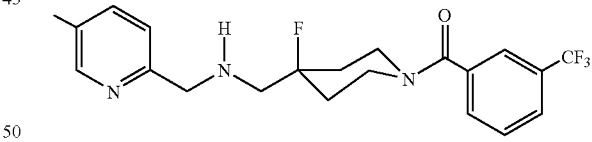

Working as in example 1, but replacing in step 1 the aldehyde (IIa-4) with 5-methylpyridine-2-carbaldehyde (IIa-1) and the primary amine (IIIa-1) with (4-aminomethyl-4-fluoropiperidin-1-yl)(3-trifluoromethylphenyl)methanone (IIIa-7), the title compound is obtained.

Dihydrochloride of the title compound:

m.p.: 172° C. (sublimation)

$C_{21}H_{25}Cl_2F_4N_3O$: 482.35

Calculated %: C 52.29; H 5.22; N 8.71

Found %: C 52.56; H 5.47; N 8.51

$^1$H NMR (DMSOd$_6$) δ: 1.83-2.08 (m, 4H); 2.37 (s, 3H); 3.08-3.51 (m, 3H); 3.28 (d, 2H); 4.36 (s, 1H); 4.37 (s, 2H); 7.66-7.88 (m, 6H); 8.57 (s, 1H).

Pharmacological Study of the Products of the Invention

Measurement of the affinity of the compounds in the invention for the 5-HT$1_A$ receptors Protocol The in vitro affinity of the compounds of the invention for the 5-$HT_{1A}$ receptors was determined by measuring the displacement of [$^3$H]8-OH-DPAT (TRK 850; 160-240 Ci/mmol).

The study of the binding to the 5-$HT_{1A}$ receptor is performed as described by Sleight and Peroutka (*Naunyn-Schmiedeberg's Arch. Pharmaco.* 1991, 343, 106). For these experiments, rat cerebral cortices are used. After thawing the brain in Tris-HCl buffer (50 mmol, pH=7.4) at 25° C., the cerebral cortex is removed and homogenized in 20 volumes of buffer maintained at 4° C. The homogenate is centrifuged at 39 000×g for 10 minutes, and the centrifugation pellet is suspended in the same volume of buffer and recentrifuged. After resuspending under the same conditions, the homogenate is incubated for 10 minutes at 37° C. and then recentrifuged. The final pellet is suspended in cold Tris-HCl reaction buffer (50 mmol) at 25° C. containing 10 mmol of pargyline, 4 mmol of $CaCl_2$ and 0.10% of ascorbic acid. The final concentration of tissue in the incubation medium is 10 mg/tube.

The reaction tubes contain 0.10 ml of [$^3$H]8-OH-DPAT (0.20 mmol final), 0.10 ml of test product 6-7 concentrations and 0.80 ml of tissue. The nonspecific binding is defined by using 10 mmol of serotonin. The reaction tubes are incubated at 23° C. for 30 minutes and their content is then rapidly filtered under vacuum through Whatman GF/B filters, and the tubes are rinsed with twice 5 ml of tris-HCl buffer at 25° C. The radio-activity collected on the filter is analyzed by liquid scintillation, by adding 4 ml of scintillant liquid (Emulsifier Safe, Packard, Warrenville, USA). All the experiments are performed in triplicate.

Measurement of the affinity of the compounds of the invention for the $D_2$ receptors Protocol The in vitro affinity of the compounds of the invention for the dopaminergic $D_2$ receptors was determined by measuring the displacement of [$^3$H]YM-09151-2 (NET-1004 70-87 Ci/mmol). The study of the binding to the $D_2$ receptor is performed as described by Niznik (*Naunyn-Schmiedeberg's Arch. Pharmacol. methods* 1985, 329, 333). For these experiments, rat striatum is used. After thawing the brain in Tris-HCl buffer (50 mmol, pH=7.4) at 25° C., the striatum is removed and homogenized in 40 volumes of buffer maintained at 4° C. The homogenate is centrifuged at 20 000×g for 10 minutes, and the centrifugation pellet is suspended in the same volume of buffer and recentrifuged. The final pellet is suspended in cold Tris-HCl reaction buffer at 25° C. containing 120 mmol of NaCl and 5 mmol of KCl. The final concentration of tissue in the incubation medium is 2 mg/tube. The reaction tubes contain 0.20 ml of [$^3$H]YM-09151-2 (0.05 mmol final), 0.20 ml of test product 6-7 concentrations and 1.60 ml of tissue. The nonspecific binding is defined by using 1 mmol of (+)-butaclamol. The reaction tubes are incubated at 23° C. for 60 minutes and their content is then rapidly filtered through Whatman GF/B filters, and the tubes are rinsed twice with 5 ml of Tris-HCl buffer at 25° C. The radioactivity collected on the filter is analyzed by liquid scintillation, by adding 4 ml of scintillant liquid (Emulsifier Safe, Packard). All the experiments are performed in triplicate.

The inhibition constants (Ki) for the products of the invention are estimated from the displacement experiments using the nonlinear regression program (RADLIG version 4 from EBDA (Equilibrium Binding Data Analysis) (Biosoft, Cambridge, UK, McPherson, 1985). The dissociation constants for the radioactive ligands used in the calculations are 0.31 mmol for [$^3$H]8-OH-DPAT and 0.036 mmol for [$^3$H]YM-09151-2. The pKi (−log Ki) values are given in the form of the mean of at least 3 experiments.

Measurement of the Efficacy of the Compounds of the Invention

Protocol

The cells (Gibco Biocult. Laboratory, Paisley UK) are collected in phosphate buffer (pH=7.4) and centrifuged at 48 000 g for 20 minutes. The centrifugation pellet is homogenized in Hepes (20 mmol, pH=7.4) containing EDTA (10 mmol) and recentrifuged at 48 000×g for 10 minutes. The centrifugation pellet is washed twice in Hepes (10 mmol, pH=7.4) containing EDTA (0.1 mmol). The pellet is stored at −80° C. in portions of 600 to 750 μg of protein. The pellet is diluted 20-fold in Hepes (20 mmol) containing 30 μmol of GDP, 100 mmol of NaCl, 3 mmol of $MgCl_2$ and 0.2 mmol of ascorbic acid. The incubation medium contains 0.4 ml of membrane preparation and 0.05 ml of test compound. After incubation for 30 minutes at 25° C., 0.05 ml of [$^{35}$S]GTPγS (500 picomol), ([$^{35}$S]GTPγS (1100 Ci/mmol), Amersham, Les Ulis France), is added and the mixture incubated for 30 minutes. The reactions are quenched by addition of 3 ml of ice-cold Hepes (20 mmol) containing 3 mmol of $MgCl_2$ and rapid filtration through Whatman GF/B filters. The tubes are rinsed 3 times with 5 ml of Hepes buffer at 25° C. The radioactivity collected on the filter is analyzed by liquid scintillation by adding 4 ml of scintillant liquid (Emulsifier Safe, Packard). The nonspecific binding is determined in the presence of cold GTPγS. The maximum stimulation of the binding of [$^{35}$S]GTPγS is defined with serotonin (10 μmmol). All the experiments are performed in triplicate.

The compounds of the invention were compared with serotonin, buspirone, 8-OH-DPAT and compound I-66 (WO 98/22459).

Results

The compounds of formula (1) and the therapeutically acceptable salts thereof have advantageous pharmacological properties. The results of these tests are collated in the following table:

| Compound | 5-HT$1_A$ pKi | $D_2$ pKi | Selectivity 5-HT$1_A$/$D_2$ | % stimulation Maximum effect |
|---|---|---|---|---|
| 5-HT | — | — | — | 100 |
| 8-OH-DPAT | 8.8 | 6.2 | ~350 | 41 |
| (+)-8-OH-DPAT | 8.7 | 6.1 | ~350 | 59 |
| buspirone | 7.6 | 7.4 | ~1 | 22 |
| I-66 | 9.1 | <5 | >1000 | 75 |
| 1-7 | 8.3 | <5 | >1000 | 90 |
| 1-9 | 9.1 | <5 | >1000 | 100 |

The results of these tests show that the compounds of formula (1) have high affinity for the serotoninergic receptors of the 5-HT$1_A$ subtype and that they are selective for these receptors with respect to the $D_2$ receptors.

The capacity of the compounds of formula (1) to stimulate the binding of [$^{35}$S]GTPγS in a cell membrane preparation is, furthermore, very much greater than those of the reference compounds such as 8-OH-DPAT, (+)-8-OH-DPAT and buspirone. The efficacy of certain compounds of the invention is also significantly higher than that of compound (I-66), which is the most efficient agonist described in the prior art. We have also found that the efficacy of certain compounds of the invention is close to or even indiscernible from that of serotonin (5-HT).

It therefore emerges from this study that the compounds of the invention have the advantage of having a selective 5-$HT1_A$ agonist profile and are more effective than the prior-art products. In this respect, the compounds of the invention are potentially useful in the treatment of disorders, complaints or pathologies involving serotoninergic dysfunctions, for instance depression, the perception of pain and the dependence on certain substances.

The administration of the compounds of the invention may be performed orally, nasally, sublingually, rectally or parenterally. A preparation of the compounds of the invention is given hereinbelow, by way of nonlimiting example of formulation. The ingredients, and also other therapeutically acceptable ingredients, may be introduced in other proportions without modifying the scope of the invention. The term "active ingredient" used in the formulation example below refers to a compound of formula (1) or an addition salt, or optionally a hydrate of an addition salt, of the compound of formula (1) with a pharmaceutically acceptable mineral acid or organic acid.

Example of a Pharmaceutical Composition

Formula for the preparation of 1000 tablets each containing 10 mg of the active ingredient:

| | |
|---|---|
| Active ingredient: | 10 g |
| Lactose | 100 g |
| Wheat starch | 10 g |
| Magnesium stearate | 3 g |
| Talc | 3 g |

The invention claimed is:

1. A compound of general formula (1):

(1)

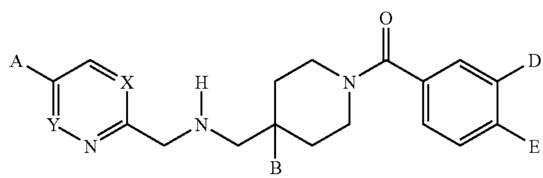

in which:

X represents a carbon atom linked to a hydrogen atom (CH) and Y represents a nitrogen atom, or X represents a nitrogen atom and Y represents a carbon atom linked to a hydrogen atom (CH);

A represents a methyl ($CH_3$), fluoromethyl ($CH_2F$), cyano (C≡N), hydroxyl (OH) or methoxy ($OCH_3$) radical or a chlorine or fluorine atom;

B represents a chlorine atom or a fluorine atom;

D represents a hydrogen atom, a chlorine atom, a fluorine atom, a cyano group (C≡N) or a trifluoromethyl group ($CF_3$);

E represents a hydrogen, fluorine or chlorine atom;

the addition salts thereof with pharmaceutically acceptable mineral acids or organic acids, and also the tautomeric forms thereof.

2. The compound of general formula (1) as claimed in claim 1, in which:

B and E each represent a fluorine atom, and

D represents a chlorine atom.

3. The derivative as claimed in claim 1, characterized in that it is chosen from the group consisting of:

(3-chloro-4-fluorophenyl)(4-fluoro-4-{[(5-methyl-pyrimidin-2-ylmethyl)amino]methyl}piperidin-1-yl)-methanone;

(3,4-dichlorophenyl)(4-fluoro-4-{[(5-methylpyrimidin-2-ylmethyl)amino]methyl}piperidin-1-yl)methanone;

(3-chloro-4-fluorophenyl)(4-fluoro-4-{[(6-methyl-pyridazin-3-ylmethyl)amino]methyl}piperidin-1-yl)-methanone;

(3,4-dichlorophenyl)(4-fluoro-4-{[(6-methylpyridazin-3-ylmethyl)amino]methyl}piperidin-1-yl)methanone;

the addition salts thereof with pharmaceutically acceptable mineral acids or organic acids, and also the tautomeric forms thereof.

4. The compound of general formula (1) as claimed in claim 2, in which A represents a methyl radical.

5. The compound of general formula (1) as claimed in claim 2, in which X represents a nitrogen atom.

6. The derivative as claimed in claim 1, characterized in that it is (3-chloro-4-fluorophenyl)-(4-fluoro-4{[(5-methylpyrimidin-2-ylmethyl)-amino]-methyl}-piperidin-1-yl)-methanone, the addition salts thereof with pharmaceutically acceptable mineral acids or organic acids, and also the tautomeric forms thereof.

7. A pharmaceutical composition, characterized in that it contains as active ingredient at least one compound as claimed in any one of claims 1 to 3, or 4-6, combined with an inert pharmaceutical support or pharmaceutically acceptable vehicle.

8. A method for the treatment of depression comprising administering to a patient in need thereof an effective amount of a compound according to any one of claims 1 to 3, or 4-6.

9. A method for the treatment of pain comprising administering to a patient in need thereof an effective amount of a compound according to any one of claims 1 to 3, or 4-6.

10. The method of claim 8 or claim 9, wherein the compound is administered by oral, nasal, sublingual, rectal, or parenteral administration.

11. The method of claim 10, wherein the administration is oral.

12. The method of claim 10, wherein the administration is parenteral.

* * * * *

UNITED STATES PATENT AND TRADEMARK OFFICE

CERTIFICATE OF CORRECTION

PATENT NO. : 7,547,700 B2
APPLICATION NO. : 10/518394
DATED : June 16, 2009
INVENTOR(S) : Vacher et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 430 days Delete the phrase “by 430 days” and insert -- by 977 days --

Signed and Sealed this

First Day of June, 2010

David J. Kappos

*Director of the United States Patent and Trademark Office*